(12) United States Patent
Friedrich

(10) Patent No.: US 9,402,937 B2
(45) Date of Patent: Aug. 2, 2016

(54) SUCTION DEVICE

(75) Inventor: Martin Friedrich, Bovenden (DE)

(73) Assignee: Georg-August-Universitaet Goettingen Stiftung Oeffentlichen Rechts (Universitaetsmedizin), Goettingen (DE)

( * ) Notice: Subject to any disclaimer, the term of this patent is extended or adjusted under 35 U.S.C. 154(b) by 252 days.

(21) Appl. No.: 13/978,429

(22) PCT Filed: Dec. 15, 2011

(86) PCT No.: PCT/EP2011/006330
§ 371 (c)(1),
(2), (4) Date: Aug. 22, 2013

(87) PCT Pub. No.: WO2012/092948
PCT Pub. Date: Jul. 12, 2012

(65) Prior Publication Data
US 2013/0324954 A1  Dec. 5, 2013

(30) Foreign Application Priority Data

Jan. 7, 2011 (DE) .................. 10 2011 008 051

(51) Int. Cl.
| | | |
|---|---|---|
| A61M 1/00 | (2006.01) | |
| A61M 5/178 | (2006.01) | |
| A61M 5/00 | (2006.01) | |
| A61M 35/00 | (2006.01) | |
| A61F 13/00 | (2006.01) | |
| A61F 13/02 | (2006.01) | |

(52) U.S. Cl.
CPC ........... *A61M 1/0031* (2013.01); *A61M 1/0025* (2014.02); *A61M 1/0033* (2014.02);*A61M1/0035* (2014.02); *A61M 2205/3344* (2013.01); *A61M 2205/3375* (2013.01); *F04B 2205/12* (2013.01)

(58) Field of Classification Search
CPC ......... A61M 1/00; A61M 5/178; A61M 5/00; A61M 35/00; A61F 13/00; A61F 13/02
See application file for complete search history.

(56) References Cited

U.S. PATENT DOCUMENTS 4,416,658 A  11/1983  Numazawa et al.
4,976,682 A  12/1990  Lane et al.
(Continued)

FOREIGN PATENT DOCUMENTS

DE   3418341 C2   11/1985
DE   196 46 410 C2   5/1998
(Continued)

*Primary Examiner* — Tatyana Zalukaeva
*Assistant Examiner* — Ilya Treyger
(74) *Attorney, Agent, or Firm* — Whitham, Curtis & Cook, P.C.

(57) ABSTRACT

The invention relates to a suction device for suctioning liquids, comprising a suction element, which is provided with at least one suction opening for receiving the liquid, and a pump which is connected to the suction element and which is equipped to generate a suction vacuum in the suction element, wherein a control device and at least one sensor which is connected to the control device are provided, wherein the control device is equipped to influence the suction power acting at the suction opening dependent on the signals received from the sensor.

Figure 1:
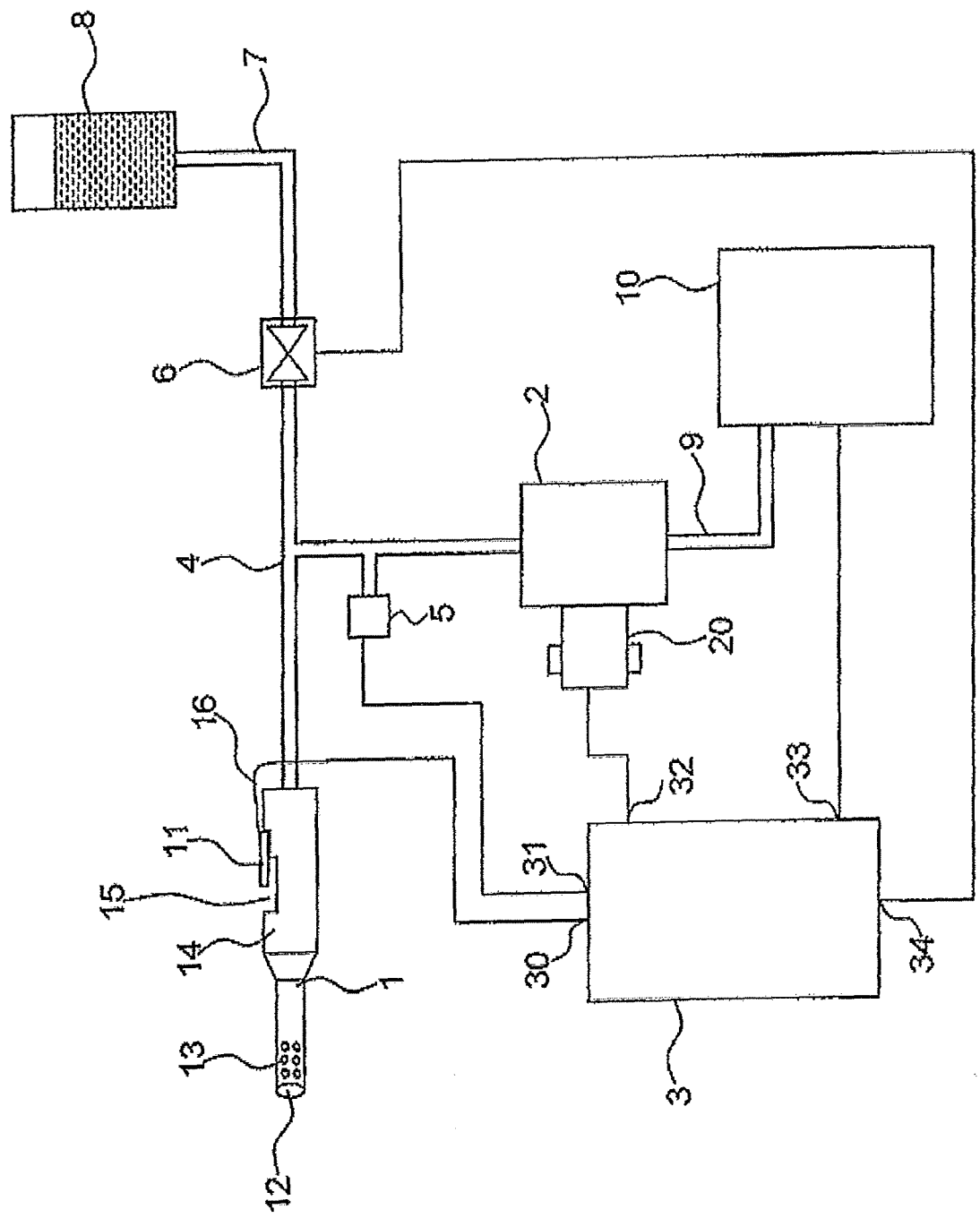

The object of the invention is to provide a suction device for suctioning liquids, said device working with greater efficiency than known suction devices. Additionally, there is a requirement in the medical field to provide a medical suction device which to the greatest possible extent prevents the damage that occurs to blood components during automatic operation.

This object is achieved by the fact that the sensor is designed as an acoustic wave sensor. The acoustic wave sensor is equipped to detect acoustic waves which are generated by the suction element during the operation thereof.

15 Claims, 3 Drawing Sheets

(56) References Cited

U.S. PATENT DOCUMENTS

| | | | | |
|---|---|---|---|---|
| 5,631,165 A | * | 5/1997 | Chupp | B01F 5/0453 422/63 |
| 5,656,499 A | * | 8/1997 | Chupp | B01F 5/0453 422/63 |
| 8,715,206 B2 | * | 5/2014 | Telfort et al. | 600/586 |
| 2010/0211029 A1 | | 8/2010 | Tsai | |

FOREIGN PATENT DOCUMENTS

| | | |
|---|---|---|
| DE | 699 23 711 T2 | 1/2006 |
| WO | WO 2007/103279 A2 * | 3/2007 |
| WO | 2007/103279 | 9/2007 |
| WO | WO 2007/103279 A2 * | 9/2007 |
| WO | 2010/075502 | 7/2010 |
| WO | WO 2010/075502 A2 * | 7/2010 |

* cited by examiner

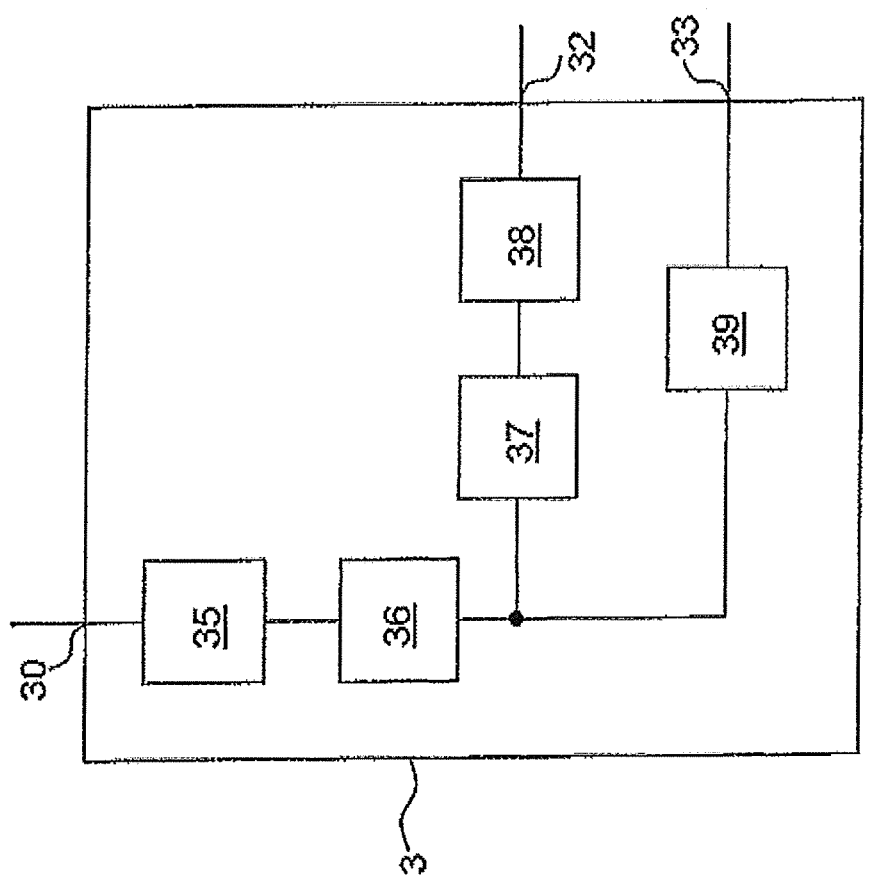

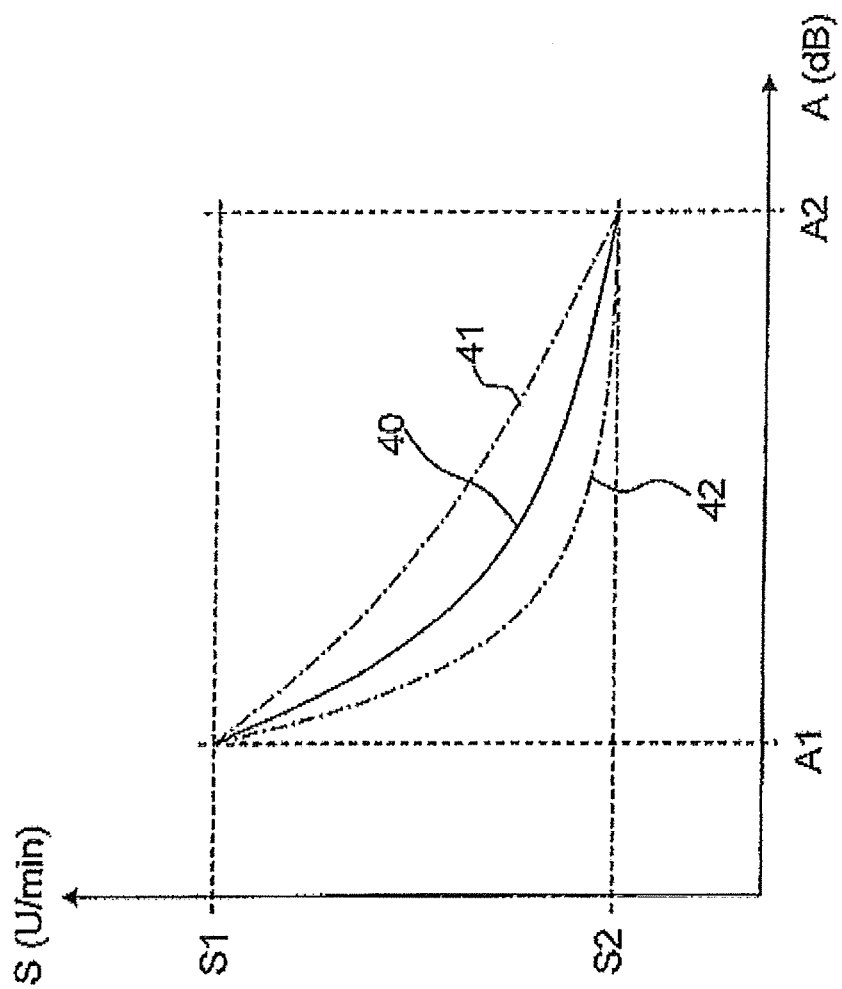

SUCTION DEVICE

The invention relates to a suction device for suctioning liquids, comprising a suction element, which is provided with at least one suction opening for receiving the liquid, and a pump which is connected to the suction element and which is equipped to generate a suction vacuum in the suction element, wherein a control device and at least one sensor which is connected to the control device are provided, wherein the control device is equipped to influence the suction power acting at the suction opening dependent on the signals received from the sensor.

A suction device of this kind can be used both in the medical field and also in the non-medical field. Therefore, possible applications in the medical field, in the form of medical suction devices, and also applications in the non-medical field are explained.

Medical suction devices of this kind are used, for example in the form of surgical aspirators, for collecting blood and other body liquids during a surgical intervention. After suitable treatment, the blood is returned to the body of a patient from whom it was taken. It is important here that the blood is gently suctioned and treated in order to avoid, as far as possible, associated overall damage affecting all the blood cells (in particular red blood cells (hemolysis) and platelets (thrombocytopathy, thrombocytopenia)) and also other blood components (proteins, messenger substances). The prior art includes proposals for automatic control of a medical suction device, which proposals can be characterized in that a suction element running empty is detected by means of a sensor. For this purpose, a pressure sensor is used according to U.S. Pat. No. 4,416,658, an optical sensor according to DE 196 46 410 C2, an air sensor according to DE 699 23 711 T2 for establishing the presence and quantity of air in the suction line, and a pressure sensor or a current sensor according to DE 34 18 341.

In practice, however, it has been found that the situations that arise in surgical practice cannot be fully covered by the known proposals. It has hitherto still been necessary for an operator who is guiding the suction element to manually influence the acting suction power or to repeatedly place the suction element again in a favorable position.

In the non-medical field too, it is desirable to operate the suction device as effectively as possible and, when suctioning liquids, to avoid undesired mixing with air from the environment.

The object of the invention is therefore to provide a suction device for suctioning liquids, said device working with greater efficiency than known suction devices. Additionally, there is a requirement in the medical field to provide a medical suction device which to the greatest possible extent avoids the damage that occurs to blood components during automatic operation.

This object is achieved by the fact that the sensor is designed as an acoustic wave sensor. The acoustic wave sensor is equipped to detect acoustic waves which are generated by the suction element during the operation thereof. Here, the expression acoustic waves comprises acoustic oscillations and vibrations of all kinds, e.g. noises. Advantageous embodiments of the invention are set forth in the dependent claims.

Advantages, possible applications and developments of the invention, both for the medical field and for the non-medical field, are explained below. The medical field is dealt with first.

According to the invention, the acoustic wave sensor receives acoustic waves that are generated by the suction element. In surgical practice, it has in fact been found that operating states of the suction element in which the aforementioned damage to the blood cells often occurs, in particular hemolysis, can easily be detected acoustically by the persons present during a surgical intervention, specifically on the basis of particular, characteristic sounds, e.g. a particularly distinct slurping suction sound. Such a sound can be detected by an acoustic wave sensor and an associated control device. As acoustic wave sensor it is possible, for example, to use a measurement microphone, or a microphone with directional characteristic, which is oriented in the direction of the suction opening.

In this way, a control of the suction element can be achieved that avoids the turbulences that damage the blood during suction, with the typical slurping suction sound being avoided. The invention has the further advantage that, for the purpose of operating the suction device, it is not constantly necessary, as hitherto, for a second assistant to be permanently present during an operation. Instead, the suction device can be operated substantially automatically.

The suction element can have one suction opening or a plurality of suction openings, e.g. one or more front suction openings and one or more lateral suction openings. As acoustic wave sensor, it is possible to use all sensors that permit detection of acoustic oscillations and vibrations of all kinds.

According to an advantageous development of the invention, the control device and/or the acoustic wave sensor are equipped to detect at least one predetermined characteristic acoustic wave pattern on the basis of the detected acoustic waves and, when such a characteristic acoustic wave pattern is detected, to change the suction power acting at the suction opening. The function for the detection of the characteristic acoustic wave pattern can be provided in the control device or in the acoustic wave sensor or distributed in both devices, e.g. on the basis of frequency filters and/or an electronic signal processing of the detected acoustic waves. For this purpose, certain acoustic wave patterns that typically arise in slurping suction sounds can be stored as comparison patterns, e.g. in the control device. The comparison patterns are then compared with the detected acoustic waves. If there is a certain degree of correspondence, a characteristic acoustic wave pattern is then regarded as detected.

According to an advantageous development of the invention, the control device is equipped, upon detection of such a characteristic acoustic wave pattern, to reduce the suction power acting at the suction opening. This has the advantage that the body liquid is sucked less rapidly to the suction opening and into the suction element, such that the red blood cells in particular impact boundary surfaces less violently. In this way, hemolysis can be considerably reduced. Further advantages include the avoidance of eddying, turbulence and acceleration at boundary structures and a reduction in the shear forces that occur. It is also advantageous that mixing of the suctioned liquids with air is avoided or at least reduced. In this way, foaming can be reduced, and undesired effects from different surface tensions can be lessened.

The acoustic wave sensor can in principle be placed at any desired location, in which respect it is of course necessary to ensure that the distance from the suction element is not too great, so that the characteristic acoustic wave patterns to be detected can be safely registered. It is possible, for example, to arrange a measurement microphone separately on a stand alongside the operating table. According to an advantageous development of the invention, the acoustic wave sensor is arranged on the suction element, on the suction side of the pump, or on a connection between the suction element and the pump. The acoustic wave sensor can also be arranged in the suction element, in the pump or in the connection between suction element and pump. In this way, the acoustic wave sensor is arranged in a certain predefined relationship to the suction device that permits a favorable positioning in respect of the detection of the characteristic acoustic wave patterns. In particular, the acoustic wave sensor is not provided separately and apart from the suction device, and instead is connected fixedly or releasably thereto in a predefined and therefore specific manner. In particular, the acoustic wave sensor can be secured fixedly on the aforementioned elements of the suction device, in particular on the suction element. It is also advantageous for the acoustic wave sensor to be secured by means of a releasable plug connection. Here, the acoustic wave sensor can advantageously be designed such that it can be secured releasably on the suction element by means of the plug connection.

According to an advantageous development of the invention, acoustic waves in the frequency range above 11 kHz are detected as characteristic acoustic wave patterns. It is likewise advantageous that acoustic waves in the frequency range above 15 kHz are detected as characteristic acoustic wave patterns. According to an advantageous development of the invention, acoustic waves in a frequency range of up to at most 50 kHz are detected as characteristic acoustic wave patterns. It has been found that, by detecting acoustic waves in these frequency ranges, a reliable separation and detection of the slurping sounds is possible, even against secondary and background noises. To detect the acoustic waves in said frequency ranges, it is possible, for example, to use a high-pass filter or a band-pass filter.

According to an advantageous development of the invention, the acoustic wave sensor is designed as a piezoelectric sensor, which is secured on the suction element. It has been found that a reliable detection of the characteristic slurping sounds can thus be achieved in a simple and inexpensive manner. Oscillations of the suction element are detected directly by the piezoelectric sensor. According to an advantageous development of the invention, the piezoelectric sensor is secured on the suction element so as to be freely oscillating at least in part. This permits a further improved detection of the acoustic waves. By virtue of the partially freely oscillating attachment of the piezoelectric sensor, the latter can be excited to stronger oscillations than if it were secured over its entire surface area on the suction element. In this way, the detection sensitivity for detecting the characteristic acoustic wave patterns is improved.

According to an advantageous development of the invention, the control device and/or the acoustic wave sensor can be connected to a blood treatment device, which is provided for treating the blood for return to the body of the patient. The blood treatment device is equipped such that the acoustic waves detected by the acoustic wave sensor and/or the detected characteristic acoustic wave patterns are used in the determination of a hemolysis score. By means of the hemolysis score, the blood treatment in the blood treatment device is controlled such that the hemolysis is substantially compensated, e.g. by separation of cell debris, fat particles or clots. According to an advantageous development, the hemolysis score includes the running time of a heart-lung machine, and the cumulative times during which characteristic acoustic wave patterns were detected. Therefore, the times at which slurping of the suction element was detected directly influence the blood treatment. The characteristic acoustic wave patterns can be included, for example, in the form of a time integral in which the amplitude of the acoustic waves is also taken into account.

A further advantageous development of the invention concerns the case where the suction element more or less adheres by suction. This poses a particular problem especially in the suctioning and relief of the left ventricle.

According to an advantageous development of the invention, at least one adherence-suction sensor is provided which is connected to the suction element, to the pump or to a connection therebetween, in such a way that an adherence suction of the suction element can be registered. Adherence suction is understood as a complete or substantial blockage or closure of the suction element, e.g. by solid particles in the liquid or by other solid or tough elements in the surrounding area, such that further suctioning of liquid is prevented at least to a large extent. Such automatic detection of the adherence suction of the suction element likewise allows countermeasures to be taken automatically, as is described below.

It will be noted that a suction device having the features of the preamble of claim 1 is also an invention in itself if at least one adherence-suction sensor is provided which is connected to the suction element, to the pump or to a connection therebetween, in such a way that an adherence suction of the suction element can be registered. The same applies to the developments mentioned below.

The adherence suction can be detected on the basis of the signal from the adherence-suction sensor, e.g. on the basis of certain characteristic signal values or on the basis of a characteristic time line of the signal, which are each characteristic of adherence suction. Thus, for example, a particular dynamic of the signal in the time course of an adherence suction process can be taken as a basis for a detection algorithm.

According to an advantageous development of the invention, the adherence-suction sensor is connected to the control device. The control device is equipped to register the signal from the adherence-suction sensor and, upon detection of an adherence suction of the suction element, to reduce the suction power acting at the suction opening. In this way, a suction element that is adhering by suction can be quickly released again. A further advantage is that the suction element can be left at the deepest point in the operating site and does not necessarily have to be moved in order to be released. This permits automated suctioning without an assistant. In particular, the suction power acting at the suction opening can be switched off for a predetermined time. It is also advantageously possible to operate the pump in reverse for a predetermined time, such that an overpressure in the suction element is generated, by which the suction element is able to detach itself again.

According to an advantageous development of the invention, the control device is equipped to actuate a valve device in phases of the reduction or switching-off of the suction power acting at the suction opening. The opened valve device connects the suction opening of the suction element to a source of liquid, e.g. to a container containing physiological saline solution. The valve device can be designed, for example, as a relay-controlled spring clip or as a solenoid valve. In this way, a closed system is created by which contamination from the outside can be avoided. It is also possible in this way to avoid undesired entry of air into the system of the suction device.

According to an advantageous development of the invention, the adherence-suction sensor is designed as a pressure sensor which is connected to the suction element, to the suction side of the pump or to a connection therebetween, in such a way that the vacuum generated by the pump can be registered. The control device is equipped to evaluate the pressure registered by the pressure sensor and to detect an adherence suction of the suction element when a predetermined pressure value is not reached and/or when a time profile of the pressure typical of an adherence suction is detected. The predetermined pressure value can be, for example, 300 mmHg, i.e. a vacuum of 2.25 Pa.

According to an advantageous development of the invention, the adherence-suction sensor is designed as a current sensor which detects the current consumption of an electric motor provided for driving the pump. The control device is equipped to evaluate the current registered by the current sensor and to detect an adherence suction of the suction element when a predetermined current value is exceeded and/or when a time profile of the current typical of an adherence suction is detected. The predetermined current value or the typical time profile of the current can be established as a function of the electrical characteristics of the electric motor used.

All of the aforementioned embodiments of the invention have in common that the change or the reduction in the suction power acting at the suction opening can take place in different ways. One possibility is that the effective pumping power of the pump is influenced, e.g. by corresponding adjustment of the operating voltage of an electric motor provided for driving the pump. A further possibility is that a bypass is switched in, e.g. in such a way that the input of the pump is connected wholly or completely to the output of the pump. Finally, a further possibility is that the suction element or a connection of the suction element to the pump, e.g. a tube, is completely or partially shut off, e.g. by an electrically actuated valve. It is likewise possible that the suction opening is changed in terms of its cross section or closed, e.g. by an automatically actuated closure cap. Combinations of the aforementioned possibilities for changing or reducing the suction power acting at the suction opening can also be advantageously realized.

In addition to the medical applications explained above, the invention can also be advantageously used, in all its embodiments, for other medical applications, e.g. in the field of dentistry. In addition to the suctioning of blood and body liquids, the suction device can also be used for the suctioning of rinsing liquid.

According to an advantageous development of the invention, the suction device of the above-described type is designed as a medical suction device. The medical suction device is equipped in particular for the suctioning of blood and/or other body liquids during a surgical intervention.

The suction device can also advantageously be used in the non-medical field, e.g. as a suction appliance for waste water, a wet vacuum cleaner, submersible pump or fire-fighting pump. The suction device can also be used for the suctioning of oil when changing the oil in an automobile, or correspondingly for the suctioning of other liquids from an automobile. In a use as a waste water suction device (waste water pump), blockage of the suction element may be caused, for example, by quite large, solid components in the water, i.e. by dirt particles. These components can cause an adherence suction, which would lead to undesired stopping or choking of the suction power. In this situation too, the invention can provide help. The same applies to wet vacuum cleaners and submersible pumps which, for example, may undesirably draw in ambient air or dirt. The resulting undesired effects can be avoided by the invention or at least significantly reduced. In the case of fire-fighting pumps, comparable problems may arise, for example when water for fighting a fire is drawn from very contaminated fire-water ponds.

The invention is explained in more detail below on the basis of an illustrative embodiment and with reference to drawings, in which:

FIG. 1 shows a medical suction device in a schematic view,
FIG. 2 shows a control device in a schematic view, and
FIG. 3 shows a control characteristic in respect of the suction power acting at the suction opening.

In the figures, identical reference signs are used for elements corresponding to one another.

FIG. 1 shows, as parts of a medical suction device, a suction element 1, a pump 2, a control device 3 and a pressure sensor 5. Also connected to the medical suction device are a valve device 6, a reservoir 8 with physiological saline solution, and a heart-lung machine 10. The suction element 1, the valve device 6, the pressure sensor 5 and a suction side of the pump 2 are interconnected by a tube arrangement 4, which among other things establishes a connection between the suction element 1 and the pump 2. The valve device 6 is connected at its other side to the reservoir 8 via a tube 7. Moreover, a delivery side of the pump 2 is connected to the heart-lung machine 10 via a tube 9.

The pump 2 has an electric motor 20 for driving the pump. When the electric motor 20 is running, the pump 2 generates, on its suction side connected to the tube arrangement 4, a vacuum by means of which body liquids can be suctioned via the suction element 1 through the tube arrangement 4. The suctioned body liquids are output from the pump 2 on the delivery side through the tube 9 and fed to the heart-lung machine 10. In the heart-lung machine 10, the body liquid fed to it is treated by a blood treatment device integrated in the heart-lung machine 10. The blood treatment device has a specially designed filter, by means of which a volume fraction of the blood is temporarily stored in a collecting basin integrated in the heart-lung machine 10.

The suction element 1 has a grip area 14 designed to allow the suction element 1 to be gripped by hand. Extending from the grip area 14 there is an elongate and narrow suction tube which, at the distal end, has a front suction opening 12 and a plurality of laterally arranged suction openings 13. In the grip area 14, the suction element 1 has a recess 15 which, for example, can be of a stepped design. A piezoelectric sensor 11, which serves as an acoustic wave sensor, is embedded in the recess 15. The piezoelectric sensor 11 is secured with only about half the extent of its length on the grip area 14, while the remaining part is freely oscillating. The piezoelectric sensor 11 is connected to the control device 3 via an electrical line 16.

The control device 3 can be designed, for example, as an electronic control system. The control device 3, of which the internal set-up is explained below, has an acoustic wave sensor input connection 30, which is connected to the piezoelectric sensor 11. Moreover, the control device 3 has a pressure sensor input connection 31, which is connected to the pressure sensor 5 via an electrical line. The control device 3 also has a pump control output connection 32, which is connected to the electric motor 20 of the pump 2 via an electrical line. The control device 3 has a hemolysis score output connection 33, which is connected to the heart-lung machine 10 via an electrical line. Moreover, the control device 3 has a valve device output connection 34, which is connected to the valve device 6 via an electrical line. Instead of the electrical lines, wireless connections can also be provided, e.g. radio connections.

The control device 3 receives the signals of the piezoelectric sensor 11 via the acoustic wave sensor input connection 30. The control device 3 receives the pressure signals of the pressure sensor 5 via the pressure sensor input connection 31. The control device 3 controls the pumping power of the pump 2 via the pump control output connection 32 and, consequently, the suction power acting at the suction opening 12, 13. The control of the pump 2 can be effected by influencing the operating voltage of the electric motor 20 or by controlling the speed of the pump 2.

The control device 3 evaluates the signals received from the piezoelectric sensor 11 and from these calculates the hemolysis score. Moreover, the control device 3 determines from this a target speed for the pump 2, which is used to control the electric motor 20. In this way, the undesired slurping of the suction element 1 is avoided. The control characteristic is explained below with reference to FIG. 3.

By way of the hemolysis score output connection 33, the control device 3 sends respectively current data for the hemolysis score to the heart-lung machine 10, which processes these data and accordingly incorporates them into the blood treatment procedure. By way of the valve device output connection 34, the control device 3 controls the valve device 6 via an electrical signal. For this purpose, the valve device 6 can be designed for example as a solenoid valve or as a relay-controlled spring clip. The valve device 6 can be opened or closed by the signal from the control device 3. In the opened state, liquid flows from the reservoir 8 through the tube 7 into the tube arrangement 4 and in this way through the suction element 1 to the suction openings 12, 13. In the closed state of the valve device 6, the connection between the tube 7 and the tube arrangement 4 is shut off.

The tube arrangement 4 can also be connected to the heart-lung machine 10. In this case, temporarily stored blood from the collecting basin of the heart-lung machine 10 or from the venous system of the heart-lung machine 10 can also be used be fed into the tube arrangement 4 for pressure compensation, i.e. a transiently opened short-circuit connection is produced.

The control device 3 also checks the pressure values delivered by the pressure sensor 5. If the pressure values fall below a vacuum of 2.25 mbar, the control device 3 stops the pump 2 and opens the valve device 6. After a predetermined time has elapsed or when a suitable pressure level has been reached, the control device 3 closes the valve device 6 again and switches the pump 2 on again. In this way, the adherence suction of the suction element 1 can be cancelled.

FIG. 2 shows an example of an internal set-up of the control device 3 with further details. The signal received at the acoustic wave sensor input connection 30 is fed to a pre-amplifier 35. Here, a relatively high-resistance pre-amplifier with an input impedance of at least 10 mega-ohms is advantageously used. The output signal of the pre-amplifier 35 is fed to a high-pass filter 36 with a frequency range above 11 kHz, in particular above 15 kHz, and up to at most 50 kHz. The output signal of the high-pass filter 36 therefore contains only frequency components above 15 kHz. This output signal is fed to a noise gate 37. The noise gate has the function of providing an adjustable delay until a response. In addition, the noise gate 37 has the function of an adjustable response threshold, i.e. a minimum amplitude of the acoustic waves. In this way, a minimum time and minimum intensity of the input signals of the noise gate 37 can be adjusted as control signal, such that it is possible to establish the acoustic wave intensity and acoustic wave duration starting from which the suction power is to be influenced. Thus, the influence of the signals of the acoustic wave sensor 11 on the function of the pump 2 is limited to signals which are present for a certain minimum time and with a certain minimum intensity, such that transient signals or signals with low intensity do not cause an undesired change in the suction power of the pump 2. The output signal of the noise gate 37 is fed to an amplifier 38 with adjustable amplification. The output signal of the amplifier 38 is then fed to the electric motor 20 of the pump 2 via the pump control output connection 32. Here, the amplifier 38 advantageously has an inverting characteristic, as is described below with reference to FIG. 3.

The output signal of the high-pass filter 36 is also fed to a microprocessor 39. The microprocessor 39 calculates the time integral from the signal amplitudes output over time from the high-pass filter 36. The respectively current value of the time integral is output from the microprocessor 39 via the hemolysis score output connection 33.

FIG. 3 shows advantageous control characteristics of the control device 3. Here, the amplitude A of the output signal of the high-pass filter 36 is shown on the abscissa, e.g. in decibels (dB). The speed S to be set for the pump 2 is shown on the ordinate, e.g. in revolutions per minute (rpm). It can be seen that the pump 2 is influenced only when the amplitude A exceeds the value A1. At lower amplitudes, the speed of the pump 2 is not influenced by the control device 3. When the lower limit value A1 is exceeded, the speed S between an upper value S1 and a lower value S2 is influenced by the control device 3. An inverting control characteristic is provided here, e.g. according to the profile 40. When the lower limit value A1 is exceeded and the amplitude A increases, the speed S is reduced from the upper value S1 toward the lower value S2. The value S2 is reached at an upper limit value A2 for the amplitude A. Depending on the application, other control curves are also conceivable, as are shown, for example, by the profiles 41, 42.

The invention claimed is:

1. A suction device for suctioning liquids, comprising:
a suction element, which is provided with at least one suction opening for receiving the liquid;
a pump which is connected to the suction element and which is equipped to generate a suction vacuum in the suction element;
a control device; and
at least one sensor which is connected to the control device, wherein the control device is equipped to influence suction power acting at the at least one suction opening of the suction element dependent on signals received from the sensor,
wherein the at least one sensor is an acoustic wave sensor which is equipped to detect acoustic waves which are generated by the suction element, wherein an output signal of the at least one sensor is fed to a preamplifier and then to a noise gate which provides an adjustable delay and an adjustable response threshold so as to establish an acoustic wave intensity and an acoustic wave duration starting from which the suction power is to be influenced by the control device.

2. The suction device as claimed in claim 1, wherein the control device and/or the at least one sensor are equipped to detect at least one predetermined characteristic acoustic wave pattern on the basis of the detected acoustic waves and, when such a characteristic acoustic wave pattern is detected, to cause a change to the suction power acting at the at least one suction opening.

3. The suction device as claimed in claim 2, wherein the control device is equipped, upon detection of the predetermined characteristic acoustic wave pattern, to cause a reduction to the suction power acting at the at least one suction opening.

4. The suction device as claimed in claim 1, wherein the at least one sensor is arranged on the suction element, on a suction side of the pump, on a connection between the suction element and the pump, or in the suction element, in the pump or in the connection there between.

5. The suction device as claimed in claim 1, wherein acoustic waves in a the frequency range above 11 kHz are detected by said at least one sensor as characteristic acoustic wave patterns.

6. The suction device as claimed in claim 5, wherein acoustic waves in a frequency range of up to 50 kHz are detected by said at least one sensor as characteristic acoustic wave patterns.

7. The suction device as claimed in claim 1, wherein the at least one sensor is a piezoelectric sensor, which is secured on the suction element.

8. The suction device as claimed in claim 7, wherein the at least one sensor is freely oscillating at least in part on the suction element.

9. The suction device as claimed in claim 1, further comprising at least one adherence-suction sensor connected to the control device, to the suction element, to the pump or to a connection there between, in such a way that an adherence suction of the suction element is registered.

10. The suction device as claimed in claim 9, wherein the adherence-suction sensor is connected to the control device, wherein the control device is equipped to register a signal from the adherence-suction sensor and, upon detection of an adherence suction of the suction element, to reduce the suction power acting at the at least one suction opening by switching off, for a predetermined time, the suction power acting at the at least one suction opening.

11. The suction device as claimed in claim 10, wherein the control device actuates a valve device in phases of the reduction or switching-off of the suction power acting at the at least one suction opening, wherein the valve device, when opened, connects the at least one suction opening of the suction element to a liquid source.

12. The suction device as claimed in claim 9, wherein the adherence-suction sensor is a pressure sensor which is connected to the suction element, to a suction side of the pump or to a connection therebetween, in such a way that the vacuum generated by the pump can be registered, and the control device is equipped to evaluate the pressure registered by the adherence-suction sensor and to detect an adherence suction of the suction element when a predetermined pressure value is not reached and/or when a time profile of a pressure typical of an adherence suction is detected.

13. The suction device as claimed claim 9, wherein the adherence-suction sensor is a current sensor which detects current consumption of an electric motor which drives the pump, and wherein the control device is equipped to evaluate the current registered by the sensor and to detect an adherence suction of the suction element when a predetermined current value is exceeded and/or when a time profile of current typical of an adherence suction is detected.

14. The suction device as claimed in claim 1, wherein the suction power acting at the at least one suction opening is effected by influencing the pumping power of the pump, by switching in a bypass, by at least partially shutting off the suction element or a connection of the suction element to the pump, and/or by changing or closing the at least one suction opening.

15. The suction device as claimed in claim 1, wherein said suction device is configured as a medical suction device for suctioning blood and/or other body liquids during a surgical intervention.

\* \* \* \* \*